United States Patent [19]

O'Lear et al.

[11] Patent Number: 5,240,681
[45] Date of Patent: Aug. 31, 1993

[54] APPARATUS FOR INJECTION ANALYSIS OF TOTAL INORGANIC PHOSPHATE

[75] Inventors: Christina O'Lear, Hickory; Keith J. Salamony, Clairton, both of Pa.

[73] Assignee: Calgon Corporation, Pittsburgh, Pa.

[21] Appl. No.: 766,237

[22] Filed: Sep. 24, 1991

Related U.S. Application Data

[63] Continuation-in-part of Ser. No. 745,638, Aug. 15, 1991, which is a continuation-in-part of Ser. No. 597,650, Oct. 15, 1990, abandoned.

[51] Int. Cl.$^5$ ................ G01N 21/08; G01N 35/08
[52] U.S. Cl. ...................... 422/82; 422/81; 422/82.09; 422/62; 422/67; 73/863.41; 73/864.81; 356/36; 356/442
[58] Field of Search .......... 422/62, 67, 81, 82, 422/82.09; 436/103; 73/863.41, 864.81; 356/36, 442

[56] References Cited

U.S. PATENT DOCUMENTS

| | | | |
|---|---|---|---|
| 3,137,543 | 6/1964 | Barton et al. | 23/230 |
| 3,796,543 | 3/1974 | Kamphake | 23/230 R |
| 3,816,075 | 6/1974 | Lambert | 23/230 R |
| 3,846,074 | 11/1974 | Tulumello et al. | 23/230 R |
| 4,645,647 | 2/1987 | Yoshida et al. | 422/81 |
| 4,826,773 | 5/1989 | Kaufman et al. | 436/105 |
| 4,952,372 | 8/1990 | Huber | 422/81 |
| 5,087,425 | 2/1992 | Flossdorf et al. | 422/81 |

OTHER PUBLICATIONS

Hirai et al Anal. Chim. Acta 115: 269-277, 1980.
Hirai et al. J. Chromatogr. 206: 501-509, 1981.
Yoza et al, Anal Chim. Acta 121: 281-287 (1980).,
Fogg et al, Analyst 108: 1485-1489 (1983).
Motomizu et al, Talanta 30:333-338 (1983).
Baba et al, J. Chromatogr 295: 153-160 (1984).
Yoza et al, J. Chromatogr 325: 385-393 (1985).
Frenzel, Fresenius' Z. Anal. Chem. 329: 668 (1988).
Clesceri et al, STD Methods for the Examination of Water & Wastewater, pp. 4-175 to 4-176 (1989).
Pederson et al, Analytica Chemica Acta, 238: 191 (1990).
Kondo et al, Corr Eng, 36: 235 (1987).
Pauer, et al Water SA 14: 125-130 (1988).
Linares et al. Anal. Chem. 58: 120-124 (1986).
Johnson & Petty, Anal. Chem. 54: 1185-1187 (1982).

Primary Examiner—James C. Housel
Assistant Examiner—David Redding
Attorney, Agent, or Firm—Raymond M. Speer; Charles M. Caruso

[57] ABSTRACT

A method for flow injection analysis of total inorganic phosphate contained in an aqueous system such as a cooling tower or boiler is described which uses a reducing agent and preservative composition therefore as the carrier for the sample to be analyzed, thereby creating a facile process which permits conversion of the various polyphosphates to orthophosphate and development of the molybdenum blue complex color reaction at 60°-95° C. and under 2-10 psi. This method has less stringent pressure and temperature requirements than those employed heretofore, thus permitting the use of more reliable and economic devices for measuring total inorganic phosphate in the field.

4 Claims, 2 Drawing Sheets

APPARATUS FOR INJECTION ANALYSIS OF TOTAL INORGANIC PHOSPHATE

REFERENCE TO RELATED APPLICATIONS

This is a continuation-in-part of application Ser. No. 07/745,638 C-15211A, filed Aug. 15, 1991, which is a continuation-in-part of application Ser. No. 597,650, filed Oct. 15, 1990, now abandoned.

BACKGROUND OF THE INVENTION

1. Field of the Invention

The present invention is in the field of methods and apparatus for flow injection analysis of total inorganic phosphate in aqueous systems. Inorganic phosphates such as orthophosphate and polyphosphate are products which are used in aqueous systems such as cooling towers and boilers to prevent calcium scales and corrosion. There is a threshold concentration at which phosphates work by causing crystal distortion that prevents calcium scale and/or steel corrosion. Thus, it is important to determine on a regular basis the concentration of dissolved inorganic phosphates so that the threshold levels necessary to prevent deposition of calcium scales is maintained. A secondary goal is to prevent high phosphate concentrations which may result in subsequent phosphate scale.

However, the analytical measurement of these inorganic phosphates is important in other fields such as environmental, clinical and agricultural analysis, where the determination of inorganic phosphate levels can also be important, as, for example, the determination of the phosphate levels in fertilizers or in clinical specimens such as plasma. The novel method of the present invention is applicable to these areas as well.

Flow injection analysis (FIA) is a well-known, simple and reliable technique based on continuous flow of a sample solution which is introduced directly into an unsegmented carrier stream of a reagent solution, thereby forming a well-defined sample zone. In so called reverse flow injection analysis, the reagent is introduced into an unsegmented sample stream. While it is being transported to a detector device further downstream, the sample has an opportunity to react with the reagent and form a new chemical species which can be quantitatively measured by the detector. The reaction is usually a color-forming one and the detector, therefore, a colorimeter (spectrophotometer). FIA lends itself to the automated, rapid and reliable analysis of various samples, and offers many advantages over the older technique of air-segmented continuous flow analysis.

Apparatus means for carrying out a typical FIA method will depend upon the reaction being carried out, but elements which are almost always present include tubing through which the samples and reagents are carried, means for moving said samples and reagents through said tubing and means for mixing them together, reagent reservoirs, means for collecting, filtering and supplying samples, heating, and analyzer means such as a colorimeter.

The color-forming reaction which has been used in the past to provide a means for quantitatively analyzing inorganic phosphate content is the well-established one wherein a mixed solution of molybdenum (V) and molybdenum (VI) reacts with orthophosphate to produce the heteropoly blue complex. It is well known that orthophosphate ($P_1$) reacts with a molybdenum (VI) reagent to form a yellow heteropoly complex and that subsequent reduction of the yellow complex by ascorbic acid or other suitable reductants gives heteropoly blue complex containing Mo(V) and Mo(VI). The formation of these heteropoly complexes has been extensively applied to the determination of phosphorus by flow injection analysis and by air-segmented flow analysis.

The total inorganic phosphate content of a sample to be analyzed will usually never be all orthophosphate; however, so that the color-forming reaction described above cannot be utilized. It is necessary to first convert the various types of inorganic phosphates present to orthophosphate in order to proceed with the flow injection analysis. Typically, the inorganic phosphates which are not orthophosphates are polyphosphates, which have the general formula $M_{x+2}P_xO_{3x+1}$, and include, e.g., pyrophosphate (diphosphate, $P_2$) and tripolyphosphate (triphosphate, $P_3$). These polyphosphates may be converted to orthophosphate by hydrolysis using concentrated sulfuric acid or other inorganic acids at high temperatures (>100° C.) and pressures for a suitable period of time, in accordance with well known procedures employed in FIA.

Typically, the acid hydrolysis reagent, e.g., concentrated sulfuric acid, is combined with the color-forming reagent, i.e., the Mo (V and VI), by dissolving the latter in the former. After the inorganic phosphates are converted to orthophosphate with this combined reagent at high temperature and pressure, and the yellow heteropoly complex is formed, in a subsequent step ascorbic acid or other reducing agent is added to the reaction mixture to form the heteropoly blue complex, which is then measured on a colorimeter.

Of course, it is also possible to use the method of the present invention to provide for the flow injection analysis of orthophosphate only, if that is desired. This may be accomplished using the same method as for polyphosphate, except that during the step of heating the reaction mixture to convert polyphosphate to orthophosphate, the reaction temperature is maintained at a lower level, sufficient for the color-forming reaction to proceed.

2. Brief Description of the Prior Art

Elemental analysis of inorganic phosphates using methods and devices other than flow injection analysis are well known; see, e.g. U.S. Pat. Nos. 3,137,543; 3,846,074; and 4,836,773.

Hirai et al., *Anal. Chim. Acta*, 115, 269–277 (1980), describe a flow injection analysis method for inorganic polyphosphates, but employ high temperatures (140° C.) and pressures (5 kg cm$^{-2}$=@ 70 psi). A solution of 0.1M L-ascorbic acid containing 50 mL of acetone is employed, but this is in a segmented flow analysis method and is used as a reducing agent for the molybdenum reagent in the color-forming step. None of this disclosure suggests the use of the ascorbic acid and acetone as a carrier stream for the sample in a flow injection analysis method as in the present invention, with the surprising advantages of lower temperature and pressure for the step of hydrolysis conversion of the polyphosphates to orthophosphate.

Hirai et al., *J. Chromatogr.*, 206, 501–509 (1981), describe a flow injection analysis method in which lower oxo acids of phosphorus such as phosphinate and phosphonate may be determined in addition to orthophosphate by oxidizing them in a solution of sodium hydrogen sulfite and molybdenum(V)-molybdenum(VI).

Yoza et al., *Anal. Chim. Acta*, 121, 281-287 (1980), describe a flow injection analysis method for the determination of polyphosphates [but only pyrophosphate ($P_2$) and tripolyphosphate ($P_3$), whereas the method of the present invention can also determine hexametaphosphate ($P_6$)] which can be carried out at room temperature because it does not involve hydrolysis conversion of the polyphosphates to orthophosphate. Quantitative determination is made by measurement of the u.v.-absorption of colored metal complexes of xylenol orange and methylthymol blue with the polyphosphates.

Fogg et al., *Analyst*, 108, 1485-1489 (1983), describe the effect of increasing ethanol and acetone concentrations on the differential-pulse voltammograms used in flow injection voltammetric determination of total phosphate at a glassy carbon electrode. This method uses manual digestion of polyphosphates, and further, would not be readily adaptable to process analysis.

Motomizu et al., *Talanta*, 30, 333-338 (1983), describe a flow injection analysis method for the determination of trace amounts of phosphate in river water using a reaction with molybdate and Malachite Green in acidic medium to form a green species. This method measures orthophosphate only at trace levels, and does not measure polyphosphates.

Baba et al., *J. Chromatogr.*, 295, 153-160 (1984), describe a parallel detection flow injection system for the simultaneous determination of phosphate and phosphonate. This method uses high pressure digestion and dual detection; whereas, the method of the present invention uses only a single channel, and is therefore less expensive to operate.

Yoza et al., *J. Chromatogr.*, 325, 385-393 (1985), describe a flow injection analysis method for determination of inorganic polyphosphates wherein they are hydrolyzed by inorganic pyrophosphatase before reaction with a molybdenum(VI) reagent for colorimetric determination. This method is applicable only to $P_3$, $P_2$, and $P_1$ species; and enzymes are unstable and would not lend themselves to continuous on-line process analysis.

Pauer, et al., *Water SA*, 14, 125-130 (1988), describe a flow injection analysis method for low concentrations of phosphate. The method uses tin chloride as a reducing agent and hydrazinium sulfate as a stablizer. The effects of injection volume, coil length and reagent concentration on optimum sensitivity are evaluated.

Linares, et al., *Anal. Chem.*, 58, 120-124 (1986) discloses analysis of binary and tenary mixtures of arsenite, arsenate and phosphate using an injection valve; mixes molybdate and ascorbic acid prior to their confluence with the sample, which is said to yield higher peaks than two sequential confluence; and uses nitric acid instead of sulfuric acid.

Johnson and Petty, *Anal. Chem.*, 54, 1185-1187 (1982) disclose a reverse flow injection analysis method in which a mixture of reagents (sulfuric acid, molybdate, ascorbic acid) are added to a sample stream; but only orthophosphate, apparently is analyzed.

SUMMARY OF THE INVENTION

In accordance with the present invention there is provided a flow injection analysis method for determination by the molybdenum blue complex colorimetric reaction of total inorganic phosphate concentration in an aqueous system containing dissolved inorganic polyphosphate as well as orthophosphate, comprising the steps of (1) establishing a filtered sample stream from said aqueous system from which sample units may be selected at designated intervals; (2) bringing together and admixing on a continuous basis the following two reagent composition streams which then form the basic flow injection analysis stream: (a) a color-forming reagent comprising an inorganic acid and molybdenum (V and VI), and (b) a reducing agent and preservative composition therefor; (3) interrupting the flow of reagent composition stream (b): a reducing agent and preservative composition therefor, and substituting therefor the filtered sample stream of step (1) for sufficient time to select a sample unit, which then becomes admixed with reagent composition stream (a): a color-forming reagent comprising an inorganic acid and molybdenum (V and VI); (4) restoring the flow of reagent composition stream (b); (5) heating the reaction mixture to 60°-95° C. for a sufficient time to effect conversion of substantially all of the polyphosphate contained in the sample unit to orthophosphate, said time also being sufficient to effect the reaction of said orthophosphate with the molybdenum (V and VI) to form a color complex; and thereafter allowing said reducing agent to partially reduce the molybdenum (V and VI) so that it has an average oxidation state between 5 and 6; (6) passing the reaction mixture containing the color complex through a colorimeter having a 600-850 nm filter and reading the signal produced thereby; and (7) from the signal information and previously available standardization data, calculating the concentration of dissolved inorganic phosphates in the aqueous stream; wherein all of the above steps are carried out under a pressure of from 2-10 psi.

The present invention may also be set forth in the manner immediately following, which describes in different terms the interaction of the sample unit and the reagent streams, which, while conceptually the same as that described immediately above, may be viewed as different in terms of the different means for carrying out that interaction. A detailed description of those different means is provided further below.

In accordance with the present invention there is provided a flow injection analysis method for determination by the molybdenum blue complex colorimetric reaction of total inorganic phosphate concentration in an aqueous system containing dissolved inorganic polyphosphate as well as orthophosphate, comprising the steps of (1) establishing a filtered sample stream from said aqueous system from which sample units may be selected at designated intervals; (2) at one said designated interval, selecting a sample unit and injecting it as a discrete unit into a continuously flowing reducing agent stream comprising a reducing agent and preservative composition therefor, so that the reducing agent stream is present in front of and behind said sample unit; (3) injecting the sample unit and reducing agent stream into a color-forming reducing agent stream comprising an inorganic acid and molybdenum (V and VI) in such manner that the sample unit and color-forming reagent are thoroughly admixed while bounded in front and behind by said reducing agent stream; (4) heating the reaction mixture to 60°-95° C. for a sufficient time to effect conversion of substantially all of the polyphosphate contained in the sample unit to orthophosphate, said time also being sufficient to effect the reaction of said orthophosphate with the molybdenum (V and VI) to form a color complex; and thereafter allowing said reducing agent to partially reduce the molybdenum (V and VI) so that it has an average oxidation state between 5 and 6; (5) passing the reaction mixture containing the color complex through a colorimeter having a 600-850 nm filter and reading the signal produced thereby; and (6) from the signal information and previously available standardization data, calculating the concentration of dissolved inorganic phosphates in the aqueous stream; wherein all of the above steps are carried out under a pressure of from 2-10 psi.

The novel interaction of the sample unit and reagent streams in the method of the present invention creates a facile process which permits conversion of the various polyphosphates to orthophosphate and development of the molybdate (V) color reaction while being carried out at 60°-95° C. and under 2-10 psi. Thus, the method of the present invention utilizes temperatures below the boiling point of water, i.e., <100° C. and significantly lower pressures than has been the case heretofore, with the attendant advantages described further below. Accordingly, it is now possible, using the method of the present invention, to develop inexpensive on-line process analyzers which permit regular and reliable determination of inorganic phosphate concentrations.

Thus, the present invention further relates to an apparatus for flow injection analysis (FIA) determination by the molybdenum blue complex colorimetric reaction of total inorganic phosphate concentration in an aqueous system containing dissolved inorganic polyphosphate as well as orthophosphate, comprising (1) filter means and three-way valve means for establishing a filtered, continuously flowing sample stream from said aqueous system to waste, from which sample units may be selected at designated intervals; (2) mixing valve means having two switchable modes of operation: (a) when a sample unit is not to be analyzed, two reagent composition streams comprising a color-forming reagent and a reducing agent, are brought together and admixed on a continuous basis; and (b) when a sample unit is to be analyzed, the stream of reducing agent is interrupted and the filtered sample stream is substituted therefor for sufficient time to select a sample unit, which then becomes admixed with the color-forming reagent stream, after which the flow of the reducing agent stream is restored; (3) a first conduit means for separately connecting and carrying the sample stream and the two reagent composition streams to said mixing valve means; (4) container means for the two reagent compositions, connected to said mixing valve means by said first conduit means; (5) a second means from said mixing valve means, and eventually to waste, for carrying the reaction mixture stream formed by mixing of the sample stream and the two reagent composition streams during and subsequent to passage through said mixing valve means, said second conduit means being of sufficient length to permit completion of the colorimetric reaction in the reaction mixture stream; (6) heating means through which the second conduit means passes for heating of the reaction mixture stream; (7) colorimetric means through which the second conduit means passes, having a 600-850 nm filter for reading the signal produced by the reaction mixture stream; and (8) means for maintaining a pressure of from 2-10 psi throughout the means comprising the FIA apparatus, whereby the sample, reagent composition, and reagent mixture streams are individually and collectively impelled through said means, eventually to waste.

In particular, the present invention relates to the FIA apparatus described above wherein the filter means is a tangential flow bypass membrane filter system; the heating means is an immersion heater; the first and second conduit means are made of polyetheretherketone tubing; and the FIA apparatus additionally includes computer means which process the data from the colorimeter means together with other data which results in calculation of the concentration of total inorganic phosphate contained in the aqueous system from which the sample for testing was obtained.

The present invention also further relates to an apparatus for flow injection analysis (FIA) determination by the molybdenum blue complex colorimetric reaction of total inorganic phosphate concentration in an aqueous system containing dissolved inorganic polyphosphates as well as orthophosphate, comprising (1) filter means, selector valve means, and injection valve means for establishing a filtered, continuously flowing sample stream from said aqueous system to waste, from which sample units may be selected at designated intervals for passage through the FIA apparatus, by switching of the injection valve means; (2) injection valve means and separate mixing connector means which are connected and operate together so as to have two switchable modes of operation: (a) when a sample unit is not to be analyzed, two reagent composition streams comprising a color-forming reagent and a reducing agent, are brought together and admixed on a continuous basis at and by the mixing connector means, the color-forming reagent flowing directly into said mixing connector means, and the reducing agent flowing into said mixing connector means after first passing through said injection valve means; and (b) when a sample unit is to be analyzed, the stream of reducing agent is interrupted by switching of said injection valve means and the filtered sample stream is substituted therefor for sufficient time to select a sample unit, which then becomes admixed, at said mixing connector means, with the color-forming reagent stream, after which the flow of the reducing agent stream is restored by switching of said injection valve means; (3) a first conduit means for separately connecting and carrying the sample stream and the reducing agent stream to said injection valve means and from there to said mixing connector means; and a second conduit means for connecting and carrying the color-forming reagent stream to said mixing connector means; (4) container means for the two reagent compositions, connected to the injection valve means and the mixing connector means by said first and second conduit means as set out above; (5) a third conduit means from the mixing connector means and eventually to waste, for carrying the reaction mixture stream formed by mixing of the sample stream and the two reagent composition streams during and subsequent to passage through said mixing connector means, said third conduit means being of sufficient length to permit completion of the colorimetric reaction in the reaction mixture stream; (6) heating means through which the third conduit means passes for heating of the reaction mixture stream; (7) colorimetric means through which the third conduit means passes, having a 600-850 nm filter for reading the signal produced by the reaction mixture stream; and (8) means for maintaining a pressure of from 2-10 psi throughout the means comprising the FIA apparatus, whereby the sample, reagent composition, and reaction mixture streams are individually and collectively impelled through said means, eventually to waste.

In particular, the present invention relates to the FIA apparatus described above wherein the filter means is a targeted flow bypass membrane filter system; the heating means is an immersionheater; the first, second and third conduit means are made of polyetheretherketone (PEEK) tubing; the mixing connector means is a T-connector; and the FIA apparatus additionally includes computer means which process the data from the colorimeter means together with other known data which results in calculation of the concentration of the total inorganic phosphate contained in the aqueous system from which to sample for testing was obtained.

DETAILED DESCRIPTION OF THE INVENTION

Figure 1:
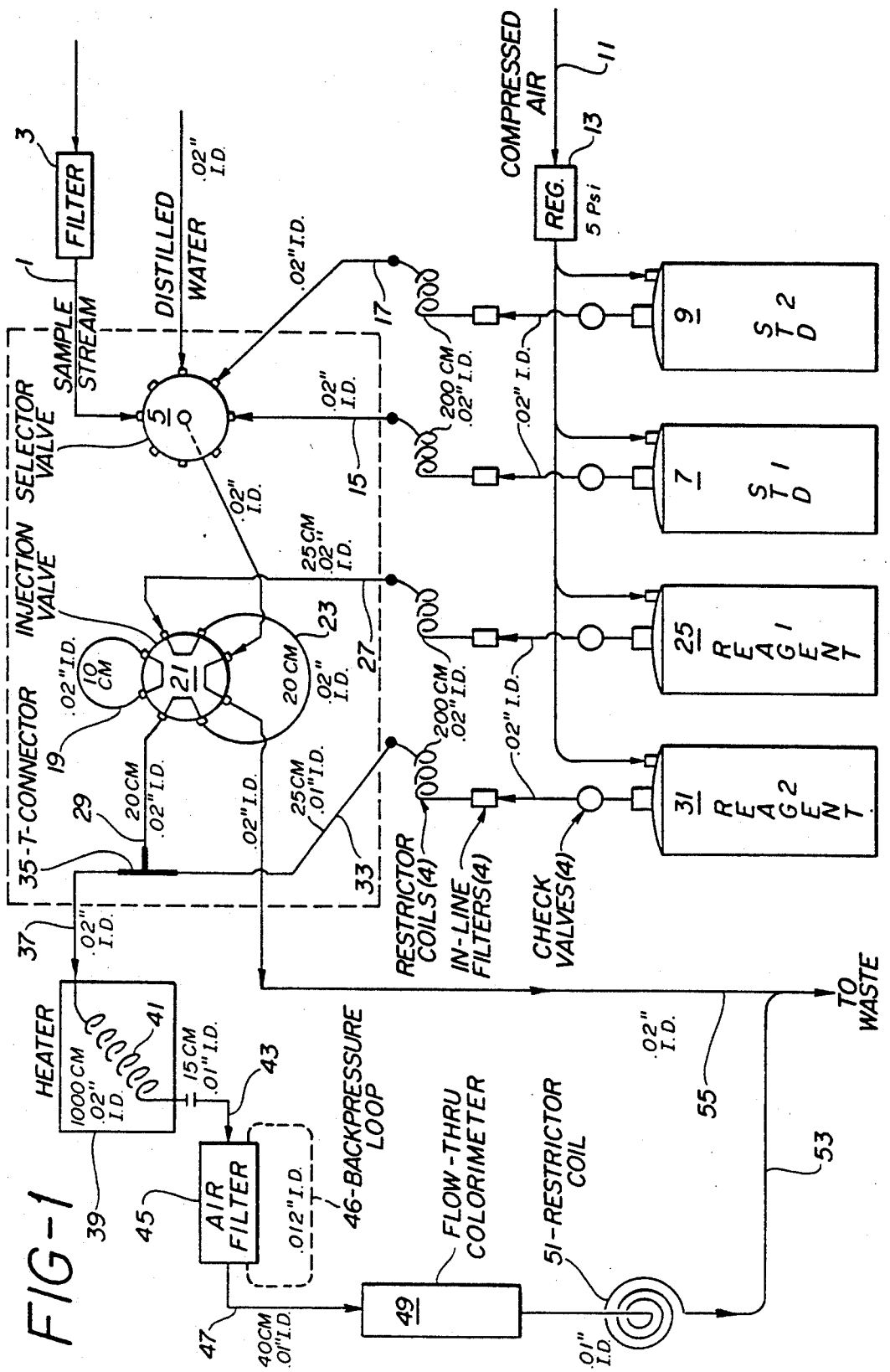
FIG. 1 is a diagram of the apparatus with the preferred embodiment of the selector valve and injection valve.

The present invention relates to a method and apparatus for flow injection analysis, a technique well known in the art. Such a method and apparatus requires a continuous flow of a sample/reagent stream in which a color reaction product is formed and read on a colorimeter. Such a method is typically carried out in an apparatus comprising a closed system in which the sample/reagent stream is carried in conduit means consisting of tubing of suitable dimensions and materials. The continuous movement of the sample/reagent stream is produced by a positive pressure accomplished by any suitable means, for example pumping means, such as a peristaltic pump, or a pressurized system in which compressed air or an inert gas such as nitrogen is used to propel the sample/reagent stream through the tubing and other apparatus means used to carry out the method. A pressurized system using compressed air is preferred. The pressure is maintained not only by the pressure of the gas source imposed on the entire system, but also by the use in combination therewith of pressure regulators, restrictor coils with reduced internal diameters, backpressure loops functioning in the same way, and the use of a semipermeable membrane through which the sample/reaction stream passes in order to remove entrained air. The use of any one or more of these devices in combination readily maintains the desired pressure throughout the flow injection analysis system.

The tubing which is used to carry the sample stream, as well as the reagent composition streams and reaction mixture invention, must be composed of a material which is able to withstand the rather harsh conditions to which it is continually subjected during the method of the present invention, including low pH, elevated temperatures and strong reagents, while maintaining dimensional uniformity within very strict tolerances, which is essential for assuring consistency and reproducibility of the analytical results over a long period of time. Materials which are subject to swelling, distention, elongation or other changes in dimensional uniformity may not be suitable for the tubing used in the apparatus of the present invention. For example, while polytetrafluoroethylene (PTFE) has many desirable features, it lacks the high degree of dimensional uniformity after extended use required for the method of the present invention. Polyethylene does not possess sufficient resistance to the low pH and reagents present in the present method. A material which has been found suitable, on the other hand, is polyetheretherketone (PEEK), and it is preferred for use with the apparatus of the present invention.

The size of the tubing is selected so as to accomplish a desired flow rate with respect to a sample size within a desired range, which makes economic use of the required reagents and affords an adequate reaction time. In the method and apparatus of the present invention, it has been found useful to employ tubing having an internal diameter (ID) of from 0.0125 to 0.1000 cm, with an internal diameter of 0.0500 cm (=0.02 in) being preferred.

Using tubing having the preferred 0.0500 cm internal diameter, a flow rate throughout the flow injection system of between 0.13 and 0.18 mL/min is maintained, preferably 0.15 mL/min. With such a flow rate, the sample unit size may vary between 10 and 150 $\mu L$, preferably between 50 and 125 $\mu L$, and most preferably 100 $\mu L$. With increasing sample unit size, it has been found that there is increasing difficulty in maintaining adequate acidity to prevent silica ($SiO_2$) interference. Silica undergoes the same color-forming reaction with the molybdate reagent employed in the method of the present invention as does orthophosphate, and thus creates the possibility of interference with the total inorganic phosphate determination. Because the color-forming reaction with silica is pH dependent, it is possible to virtually eliminate the silica interference by maintaining a sufficiently low pH. This is done most conveniently by utilizing an adequate amount of the inorganic acid, e.g., concentrated sulfuric acid, which is part of the color-forming reagent composition used in the method of the present invention.

The pressure in the system, which is preferably achieved by use of compressed air to create a pressurized system, and by means of which the flow rate described above is maintained, should be between 2 and 10 psi, preferably between 4 and 6 psi. This is a significant reduction in the amount of pressure required in many flow injection analysis methods and devices employed in the prior art, which have often used pressures as high as 70 psi. The purpose of such high pressures was to suppress the bubbling caused by the release of dissolved air in the sample/reaction mixture during travel through the colorimeter, which interfered with the readings obtained from that instrument. Such high pressures were a concomitant, however, of the use of high temperatures, i.e., >100° C., in the prior art methods to carry out the hydrolysis reaction which converted the polyphosphates to orthophosphates. It is possible, using the present invention, to avoid the high pressures of the prior art methods and devices because the corresponding high temperatures of those methods and devices have also been eliminated.

Returning to the starting point of the flow injection analysis method of the present invention, it is one for the determination of the concentration of total dissolved inorganic phosphate in an aqueous system. It has already been noted further above that the inorganic phosphate content is primarily polyphosphate. It has also been noted that the method of the present invention may be used to determine the concentration of orthophosphate only, if that is desired.

The aqueous system in its broadest context is any water solution containing dissolved inorganic phosphate which is used as a sample for analysis in the flow injection method of the present invention. Most typically, this aqueous system is water from a cooling tower or a boiler. However, the method of the present invention obviously has wider applicability, and it is intended that it include analyses where the aqueous system is, e.g., a clinical specimen, or where a sample of fertilizer has been dissolved in water for analysis using the method of the present invention.

Where the aqueous system sample is from cooling tower water or boiler water, it is usually found to contain suspended fine solids which will clog the tubing and otherwise interfere with the various pieces of apparatus used to carry out the method of the present invention. Thus, sample filtration is necessary to separate corrosion inhibiting phosphate from phosphate tied to suspended material and to prevent plugging of the instrument. Scale and corrosion inhibiting phosphate is considered to be dissolved phosphate or phosphate attached to $<0.45\mu$ sized particles. Bypass membrane filtration is preferred, with tangential entry of bypass being desirable for on-line sample filtration, because membrane fouling is slowed by the cleaning action of the sample stream. Commercial filtering systems which are suitable include the from Millipore Corp., Bedford, Mass. 01730-9903; Minitan-S filter assembly, Collins Products Company, Livingston, Tex. 77351 and the Collins Swirlclean bypass filter. Consequently, it is provided that the sample stream be filtered. Any filter material or device which will remove the suspended fine solids from the sample stream is suitable; and it has been found that good results are achieved with the method and apparatus of the present invention when particles of $0.45\mu$ and larger are removed.

It is necessary to establish the filtered sample stream in such a way that sample units may be selected therefrom at designated intervals. This is suitably carried out using a selector valve together with an injection valve, both of which are of known design and allow the sample stream, which is being filtered, to flow in a continuous manner through the selector and injection valves to waste, but not through any other part of the flow injection analysis system. In addition to assuring that a fresh sample unit is provided whenever a sample is to be analyzed, the selector valve also functions to permit the introduction of standards and distilled water into the basic flow injection analysis stream. It will be appreciated that other devices may be substituted for the selector valve, i.e., devices of known design and function which are capable of carrying out the method of the present invention, particularly that part of the method accomplished by the selector valve. One such other device is described further below.

Sample units for evaluation in the flow injection system are selected at designated intervals. These designated intervals are predetermined based on the number of samples that it is desired to test within a given period of time, and are usually preprogrammed into a computer or similar device which controls the operation of the entire flow injection analysis system. During conventional operation, the selector valve will be set so that the sample stream enters the selector valve and then goes on to the injection valve, and from there on to waste. On command from the computer or other control device, or even manually, the injection valve then directs the sample stream through a sample loop of tubing which is of the appropriate dimensions to give the desired sample size, most preferably 100 μL.

The sample loop is preferably in the separate device termed the injection valve, which has as its function the injecting of the sample unit into the continuously flowing reagent stream. The device functions in such a way that the sample unit is injected into a reagent stream. The injection of the sample unit into a reagent stream may take place in two different ways which, while accomplished by different means, are conceptually the same and thus represent different embodiments of the present invention. One such means is a mixing valve, which has two or more inlet ports and a single outlet port. Within the valve assembly, means controlled by the operation of a solenoid allow measured quantities of the contents of a tube leading to one of the inlet ports to pass through the valve assembly and out the outlet port. The solenoid then closes that inlet port and opens a second inlet port, where again a measured quantity of the contents of a tube leading to the second inlet port are allowed to pass through the valve assembly and out the outlet port. By alternating the opening and closing of these inlet ports, e.g., once a second, a thorough mixing of the contents of the two tubes entering the inlet ports is achieved.

When a mixing valve is used to carry out the method of the present invention, it functions in the following way. During the stage of the process when the basic flow injection analysis stream is moving through the system in a state of readiness to receive a sample unit to be analyzed, the two reagent composition streams which form the basic flow injection analysis stream are brought together and admixed at a mixing valve. These two reagent composition streams are (a) the color-forming reagent compromising an inorganic acid and molybdenum (V and VI), and (b) the reducing agent and preservative composition therefor. Either the timing of the solenoid which controls the amount of each reagent stream leaving the outlet port, or the concentrations of the reagent compositions themselves, may be adjusted so as to predetermine the ratio of the reagent concentrations in the basic flow injection analysis stream. These can be set as desired, depending on the makeup and stoichiometry of the reagent composition streams. For example, where concentrated sulfuric acid and ascorbic acid are used, the timing and/or concentrations are adjusted to provide a 1:1 molar ratio of the reagents.

When a sample unit is to be analyzed, the selector and injection valves are set and activated so that a sample unit travels through a tube to a third inlet port of the mixing valve described above, where it enters the mixing valve. At the same time, however, the inlet port for the reducing agent and preservative composition is closed, so that the sample unit is, in effect, substituted therefor, and as a consequence, the sample unit becomes admixed with the color-forming reagent which is still entering the mixing valve. After the sample unit has completely passed through the mixing valve, its inlet port is closed and that for the reducing agent and preservative is reopened. As a consequence of the above actions, it will also be seen that the reducing agent and preservative reagent composition is present in front of and behind the sample unit in the basic flow injection analysis stream.

Another embodiment of the present invention replaces the selector and injector valves described above with the simple expedient of a three-way valve connected by tubing directly to the mixing valve, through which sample continuously flows to waste through one of the ports of the three-way valve. By means of such a valve, it is possible to have a continuous flow of fresh sample, and then by switching the three-way valve, provide for direct flow of a sample unit to the mixing valve, the unit size being determined by the length of time that the three-way valve remains open for passage of sample.

Another means for accomplishing the injection of the sample unit into a reagent stream, involves the use of an injection valve as described above together with a T-connector. As with the mixing valve embodiment, during the stage of readiness for receiving a sample unit, the two reagent streams are mixed together on a continuous basis, but by means of being brought together at the T-connector rather than through a mixing valve. When a sample unit is to be analyzed, the injection valve is activated and the sample unit is injected into the reducing agent and preservative composition reagent stream, which also passes through the injection valve on a continuous basis. As a consequence, the reducing agent stream is present in front of and behind said sample unit, viewed as a continuously flowing system, just as with the mixing valve embodiment described further above. The reducing agent stream pushes the sample unit on ahead of it so that when the sample unit reaches the T-Connector, only sample and color-forming reagent are admixed at the T-connector, just as with the mixing valve embodiment described further above.

In both embodiments described above, as the sample/color-forming reagent mixture passes through the remainder of the flow injection analysis system, acid hydrolysis of inorganic phosphate to orthophosphate takes place and the molybdate heteropoly yellow complex is formed. During the course of this passage, the reducing agent will also completely infiltrate the mixture, forming the molybdate heteropoly blue complex. It is believed that by means of this novel series of steps, the method of the present invention is able to utilize low pressures and temperatures to accomplish the hydrolysis of dissolved polyphosphates and the color-forming reaction, which has required high temperatures and pressures in the methods of the prior art.

In both of the two embodiments for carrying out the method of the present invention, the reducing agent stream comprises a reducing agent and a preservative composition therefor. The reducing agent acts to reduce the phosphomolybdate complex to the heteropolymolybdate blue form. A commonly employed reducing agent recognized for this purpose is ascorbic acid, and this is the preferred reducing agent for use in the method of the present invention. However, other reducing agents are known in the art, and any of these, or any combination of these, may be employed. See, e.g., Frenzel, *Fresenius' Z. Anal. Chem.*, 329, 668 (1988); *Standard Methods for the Examination of Water and Wastewater*, Clesceri et al., eds. 17 Edition, p. 4-175 to 4-176 (1989): and Pederson et al., *Analytical Chemica Acta*, 238, 191 (1990). Suitable reducing agents include stannous chloride. 4-amino-3-hydroxy-1-naphthalenesulfonic acid, sodium sulfite, sodium bisulfite, and sodium metabisulfite. The amount of ascorbic acid employed will be between 10 and 30 g/L, preferably between 15 and 20 g/L.

It is possible to use a catalyst such as antimony (III) to accelerate the activity of the reducing agent, and thus the rate of reduction.

Decomposition of the reducing agent such as ascorbic acid will occur without the use of one or more preservatives. Such decomposition can be caused by dissolved oxygen in the aqueous system, or by the presence of oxygen radicals. The presence of heavy metals may also catalyze such decomposition. Preservative agents for use with the reducing agents of the present invention, and which act as oxygen scavengers, include those recognized in the art as suitable for that purpose, e.g., acetone, which is preferred, other ketones such as methylethyl ketone, glycerol (Kondo et al., *Corr. Eng.*, 36, 235, 1987), and glycol. They may be used alone or together in combination.

Chelating agents which bind to heavy metals capable of catalyzing the decomposition of the reducing agents may also be used in the preservative composition. Any chelating agent which will chelate metals which cause instability of the ascorbic acid, and which is otherwise compatible with the other elements present in the method of the present invention, may be used. A preferred chelating agent is ethylenediaminetetraacetic acid (EDTA) in any of its various salt forms, e.g., tetrasodium EDTA, edetate sodium, edetate disodium, edetate trisodium, and edetate calcium disodium. Disodium EDTA is preferred. Nitrilotriacetic acid may also be used, for example.

A preferred reducing agent and preservative composition for use in the method of the present invention has the following composition:

| 17.6 g | ascorbic acid | In 1 L of |
| 50 mL | acetone | deionized |
| 7.6 mg | disodium EDTA | water |

The disodium EDTA is conveniently added as 2 mL of Calgon Reagent R-5010, which is 0.001M EDTA and contains sufficient NaOH to solubilize the EDTA, as well as a very small quantity of a preservative.

The amount of reducing agent such as ascorbic acid employed will be between 10 and 30 g/L, preferably between 15 and 20 g/L. The amount of preservative such as acetone employed will be between 45 and 55 mL/L, preferably 50 mL/L.

In both embodiments of the method of the present invention described above, the color-forming reagent stream comprises an inorganic acid and molybdenum (V and VI). Hydrolysis of the polyphosphate to orthophosphate takes place in an acidic medium, and for this purpose there may be employed, e.g., concentrated sulfuric acid ($H_2SO_4$), which is preferred. Other suitable inorganic acids, such as hydrochloric acid (HCl) and perchloric acid ($HClO_4$) may be used, but these tend to be more volatile and fuming and/or oxidizing, as in the case of $HClO_4$, which tends to introduce some element of hazard into the flow injection analysis method. Nitric acid ($HNO_3$) may also be employed, either alone or in combination with $H_2SO_4$. However, since $HNO_3$ acts as an oxidizing agent, it can introduce complications into the overall chemistry of the flow injection analysis method.

The inorganic acid reagent, while its purpose is hydrolysis of the polyphosphate to orthophosphate, is referred to herein along with the molybdenum (V and VI) as the color-forming reagent, since these reagents are most advantageously and typically employed together.

The molybdenum blue complex reagent composition may be prepared in accordance with procedures known in the art. However, the method of the present invention does permit use of a simple molybdate reagent which is a distinct improvement over the complex molybdate reagent used by Hirai et al., and prepared as described in *Anal. Chim. Acta*, 115, 269–277. That procedure involves several steps and use of concentrated hydrochloric acid in addition to concentrated sulfuric acid, as well as use of a zinc reducing agent. By contrast, the molybdate reagent for use in the method of the present invention may be prepared simply by dissolving from 5 to 15 g, preferably 10 g of ammonium molybdate tetrahydrate [$(NH_4)_6Mo_7O_{24} \cdot 4H_2O$] in from 60 to 120 mL, preferably 102 mL of concentrated (95%) sulfuric acid ($H_2SO_4$). The solution may then be diluted to 1 L with deionized water to give the molybdenum (V and VI) reagent solution. When this reagent mixes with the reducing agent stream containing, e.g., ascorbic acid, the ascorbic acid partially reduces the molybdenum so that it has an average oxidation state between 5 and 6. The molybdenum blue color complex results.

The manner in which the color-forming reagent solution is brought into contact with the sample unit and reducing agent stream has already been described. All of these components must be thoroughly admixed to form the resultant reaction mixture in the course of their passage through the tubing of the flow injection analysis system. This can be accomplished by having the tubing carrying the sample unit and carrier stream mixture meet tubing carrying the reagent solution at a 90° angle T-connector. Other devices which accomplish the same objective of thorough admixture may be used. One such device, which retains the advantages of efficiency, reliability, and economy that characterize the T-connector, is a solenoid operated mixing valve of the type sold by Bio-Chem Valve Corp., East Hanover, N.J. Such mixing valves feature low power consumption, isolated solenoid, high cycle life, low internal volume, fast response time, Teflon wetted parts, and valve seat travels adjusted for accurate fluid sampling. The mixing valve can mix together the proper ratio of reagents and samples by switching from one stream to another in rapid succession, resulting in a well mixed solution. The very rapid mixing of samples and reagents which can be achieved with such a mixing valve results in faster reaction times and sharper peak shape from the colorimeter.

The next step involves heating of the reaction mixture so that the hydrolysis of the inorganic polyphosphates to orthophosphates may be completed. This hydrolysis or digestion step is carried out at a temperature of from 60°–95° C., and preferably from 75°–93° C., but most preferably at 90° C. Where it is desired to analyze only the content of orthophosphate in the aqueous system, then the temperature will be between 25° and 35° C., preferably 30° C. The time for this step to be completed, whether it is for total inorganic polyphosphate, or orthophosphate only, will be from 10 to 25 min, usually from 15 to 20 min. A typical residence time for completion of this step is 16 min. The device most convenient for carrying out this step is a simple reaction coil, e.g., one coil of tubing 1000 cm in length and 0.0500 cm (=0.02 in) internal diameter encased in an aluminum heater block.

Using flow rates within the range of those described above, the desired overall reaction time is achieved with such a device. Other means may be substituted for the reaction coil. It may be more economical, e.g., to change from a spool of tubing encased in an aluminum heater block to an immersion heater with a thermocouple attached to the surface of the heater and held in place by tightly rapped tubing and insulated with silicon tape. In such a device, the surface of the heater is hotter than the opposite side of the tubing by about 5° C. (heater surface temperature of about 90° C. and room temperature operation), making the sample temperature somewhere between those two values. Using more insulation reduces the temperature differential, but slows cooling rates. Using this design, heater temperatures up to about 95° C. will not boil the flow injection analysis reaction mixture.

As has already been described, the reaction which takes place in this step achieves two results: (1) the inorganic polyphosphates are converted by acid hydrolysis to orthophosphate, and (2) the orthophosphate reacts with the molybdenum (V and VI) reagent to form the heteropoly blue complex. This latter reaction is the color-forming step in which the color complex is formed. A third and ancillary reaction may also be taking place during this step; and that is completion of the partial reduction of the molybdenum (V and VI) by the reducing agent, e.g., ascorbic acid so that an average oxidation state between 5 and 6 is achieved.

Even though the reaction temperatures for the step described above are below the 100° C. boiling point of water, and it is therefore unlikely that significant amounts of dissolved air gases (oxygen and nitrogen) will come out of solution, it is preferred to employ an air filter which will remove any such bubbles of gas which may unexpectedly appear. The evolution of gas bubbles can cause unacceptable detector "noise" when the reaction mixture containing the color complex is passed through the colorimeter for reading. As already explained above, the air filter is conveniently a semipermeable membrane through which the reaction mixture is passed to remove any extraneous gases which have formed. Such air filters are well known in the art. Furthermore, because of the improvement obtained with the method of the present invention whereby lower temperatures and pressures are required than with the methods employed heretofore in the prior art, it is not necessary to employ at this stage of the method a cooling coil to reduce the temperature of the reaction mixture prior to passing it through a colorimeter.

The next step in the flow injection analysis method of the present invention involves passing of the reaction mixture containing the color complex through a colorimeter. This is typically a flow-through cell spectrophotometer equipped with a filter which permits monitoring of the heteropoly blue complex within a wavelength range of from 600 to 850 nm. A 650 nm filter is usually employed. The path length for the flow-through colorimeter cell is from 0.5 to 2 cm, but is preferably 1 cm in length.

The last step of the flow injection analysis method of the present invention is the one which utilizes the information obtained from the colorimeter reading in the preceding step and together with information already available, calculates the concentration of total inorganic phosphate contained in the aqueous system from which the sample for testing was obtained. It is desirable to employ standards and routinely test these so as to obtain and have readily available 2-point standardization data. It is most convenient to employ a computer to process all of this data and calculate the desired end result. Thus, the signal from the colorimeter may be sent directly to such a computer; and the information derived from the colorimeter reading together with the other data necessary to calculate the end result which is already stored in the computer memory, permits a very rapid and automatic readout of the concentration of total inorganic phosphates in the aqueous system on an ongoing and regular basis.

DESCRIPTION OF THE DRAWINGS

FIG. 1 of the drawings depicts a typical analyzer apparatus for carrying out the method of the present invention. The solid lines depict conduit means, i.e., tubing which carries the sample/reaction streams through the various steps of the method. The depiction is not drawn to scale, and the length of tubing may be varied unless a preferred length is otherwise specified.

Figure 2:
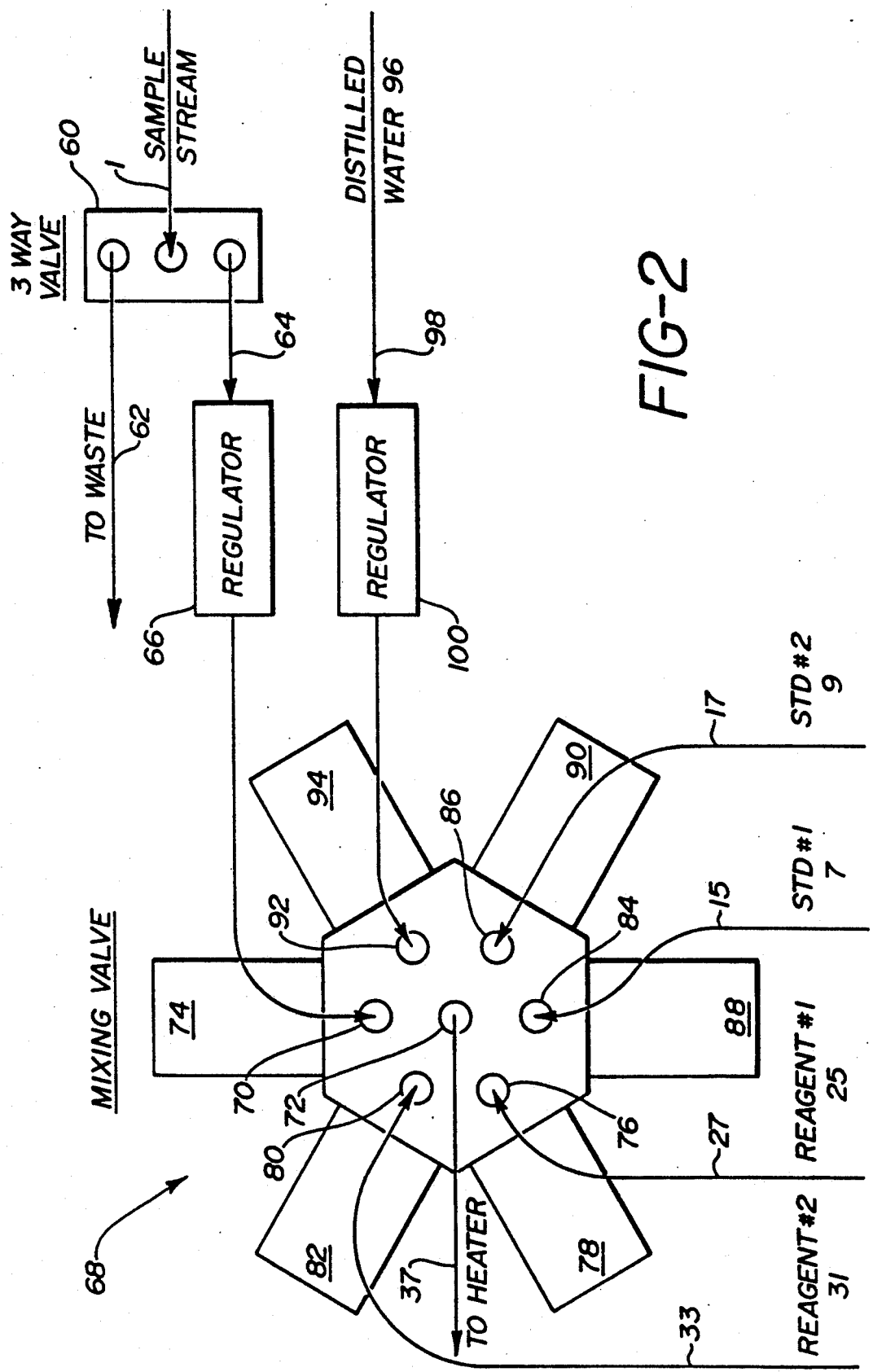
FIG. 2 illustrates the 3-way valve and mixing valve, alternatives to the selector and injection valves of FIG. 1.

The dashed lines enclose specific means in the apparatus which are replaced with other means to form the embodiment shown in FIG. 2. A sample stream 1 from an aqueous system (not shown) enters through a filter means 3 which removes suspended solids which might otherwise clog the tubing of the system.

The sample stream continuously flows through the selector valve 5, to which standard solutions 7 and 9 are also connected by tubing 15 and 17, respectively. These standard solutions operate as substitutes for the sample stream and are sent through the flow injection system on a regular basis in order to provide a set of 3-point standardization data for making the end result calculations.

Movement of the standard solutions as well as the sample stream is accomplished by use of a pressurized system, using a source of compressed air 11 under pressure regulated by regulator 13.

When a sample is analyzed, the selector valve 5 will be directing the sample stream through a sample loop 23 in injection valve 21 through tubing 55 to waste, thus assuming a continuous supply of fresh sample. At designated intervals, the injection valve 21 switches the sample in-line so that the reducing agent reagent 25 arriving through tubing 27 and previously contained in loop 23 of injection valve 21, pushes the sample unit ahead through tubing 29. Before the sample is injected, reducing agent reagent 25 flows through loop 23 and tubing 29 on a continuous basis, where it becomes admixed at T-connector 35 with color-forming reagent 31.

The pressurized containers for the standard solutions 7 and 9, as well as the reagents 25 and 31, are assisted in their function by check valves, in-line filters, and restrictor coils, but these are standard features and are not identified by numbers in the drawing.

While the sample unit is traversing tubing 29, it is bounded in front and behind by reducing agent reagent 25. This sample unit enters the T-connector 35, into which also enters tubing 33 carrying the color-forming reagent 31. Because of the "T" configuration of the junction, there results a thorough admixture of the sample unit and color-forming reagent. When the reducing agent infiltrates this admixture, the overall reaction mixture comprising the basic flow injection analysis stream is formed.

The reaction mixture is carried through tubing 37 to a heating device 39 which maintains a temperature between 60° and 95° C., and which contains a coil of tubing 41 of sufficient length to allow the required residence time of about 16 min for the reaction mixture.

The heteropoly blue complex has now been formed in the reaction mixture, and this is carried through tubing 43 and an air filter 45 to remove any air bubbles which have unexpectedly evolved during the reaction heating. Instead of an air filter 45, there may be employed at this point a backpressure loop 46.

The color complex together with the reaction mixture is now carried through tubing 47 to the colorimeter 49 containing a flow-through cell with a 650 nm filter (not shown), where the sample is read. The reading of the colorimeter 49 may be visually inspected, or may form a signal sent to a computer (not shown) which uses that and other data to calculate the concentration of inorganic polyphosphate in the sample.

A restrictor coil 51 assists in maintaining the pressure (@ 5 psi) in the system, and after passing through this coil, the reaction mixture with color complex which has now been read in the colorimeter 49, passes to waste through tubing 53.

FIG. 2 of the drawings depicts another embodiment of the apparatus of the present invention in which a three-way valve and mixing valve means have been substituted for the selector valve and injection valve means depicted in FIG. 1 of the drawings. The area of substitution is shown in FIG. 1 by means of the dashed lines. While the different means of FIG. 2 operate in a different way from the means of FIG. 1, conceptually the same functional results are obtained, i.e., the same method steps are achieved.

The filtered sample stream 1 enters a three-way valve means 60 and flows through conduit means, i.e., tubing 62 to waste on a continuous basis so as to provide fresh sample. When a sample is to be analyzed, the three-way valve 60 is switched so that a sample unit now flows through tubing 64 and pressure regulator 66 to the mixing valve means 68. The size of the sample unit is determined by the length of time that the three-way valve 60 remains switched, which is readily controlled in a predetermined manner.

The sample unit in tubing 64 enters mixing valve 68 through inlet port 70 and then exits the mixing valve through outlet port 72. The amount of sample which enters and leaves the mixing valve is determined by the opening and closing of the inlet port 70, the operation of which, in turn, is controlled by solenoid 74. Once the sample leaves the mixing valve 68, it continues on through tubing 37 to the heater 39 and other portions of the flow injection analysis system depicted in FIG. 1 of the drawings.

During the stage of the process when the basic flow injection analysis stream is moving through the system in a state of readiness to receive a sample unit to be analyzed, the two reagent composition streams which form the basic flow injection analysis stream are brought together and admixed by the mixing valve 68. The reducing agent and preservative composition reagent 25 moves through tubing 27 (as in FIG. 1) to inlet port 76 controlled by solenoid 78. The color-forming reagent 31 moves through tubing 33 (as in FIG. 1) to inlet port 80 controlled by solenoid 82. Thorough admixing of the two reagents is accomplished by the mixing valve 68 through rapid successive opening and closing of the inlet ports 76 and 80, controlled by solenoids 78 and 82, respectively. The thoroughly admixed reagents then exit the mixing valve through outlet port 72 and continue on through the remainder of the flow injection analysis system by way of tubing 37.

When the sample unit enters the mixing valve 68 through its inlet port 70, inlet port 76 for reducing agent 25 is automatically closed by solenoid 78 in accordance with a preset control program (not shown). As a result, the sample unit now becomes admixed with the color-forming reagent 31 by operation of the mixing valve 68 as described above. As soon as the sample unit has passed through the mixing valve, its inlet port 70 is closed again and inlet port 76 for reducing agent 25 is automatically reopened by the same preset control program. As a result, the reducing agent 25 will be found in front of and behind the mixture of sample unit and color-forming reagent, and these all together form the basic flow injection analysis stream which proceeds on through tubing 37 to the remaining steps and means of the flow injection analysis system depicted in FIG. 1.

Mixing valve 68 depicted in FIG. 2 has a total of six inlet ports, the function of only three of which has been described above. Use of the additional inlet ports can provide a facile substitute for the selector valve and injection valve depicted in FIG. 1 with respect to the use of standards and dilution with distilled water as well. When it is necessary to analyze the standards 7 and 9, they may be brought to mixing valve 68 through tubing 15 and 17, respectively (as in FIG. 1), and enter through inlet ports 84 and 86 controlled by solenoids 88 and 90, respectively. Their admixture with the reagents 25 and 31 takes place in the same manner as described above for the sample unit, all of which is controlled by the preset control program. Use of the remaining inlet port 92 controlled by solenoid 94 for introduction of distilled water through tubing 98 which passes through pressure regulator 100, affords a ready means of direct dilution of any of the samples, standards or reagents which enter the mixing valve 68, as described above.

The remainder of the flow injection analysis system and its function are as described further above for FIG. 1.

DESCRIPTION OF PREFERRED EMBODIMENTS

The following example provides a demonstration of a preferred embodiment for carrying out the method of the present invention, but is not intended to be in any way a limitation of that method.

A filtered cooling water stream runs to a selector valve. At designated intervals the selector valve directs the sample stream through a 10 μL sample loop in an injection valve. The injection valve switches the sample in-line so that the ascorbic acid reagent (carrier) pushes the sample ahead. The sample mixes with acid molybdate at a 90° angle T-connector. From there it enters a 1000 cm 0.02 in id heating coil at 60°-80° C. For determination of orthophosphate only, the heating coil was at 30° C. It takes 16 min for the sample to traverse the coil. It then passes through an air filter which removes extraneous air bubbles. Next the sample flows through a colorimeter with 1 cm path length and 650 nm filter. The signal is sent to a computer which calculates the data from a 2-point standardization which is repeated periodically by injecting orthophosphate standards.

The following table of values shows results obtained using the above method for cooling water, except that the sample stream was sampled individually through a sampling device rather than an incoming stream to a selector valve.

TABLE

| Sample No. | mg/L Total | mg/L Ortho | Sample No. | mg/L Total | mg/L Ortho |
|---|---|---|---|---|---|
| 3127 | <2 | <2 | 3265 | 3.8 | 2.6 |
| 3266 | 2.7 | <2 | 3288 | <2 | <2 |
| 3289 | 5.5 | 4.3 | 3425 | 2.4 | <2 |
| 3275 | 8.2 | 4.0 | 3276 | 20.7 | 12.2 |
| 3491 | <2 | <2 | 3653 | 4.3 | 3.6 |
| 3767 | 16.4 | 4.2 | 3768 | 17.4 | 5.5 |
| 3692 | 44.4 | 27 | 3892 | 8.2 | 4.7 |
| 3771 | 16.6 | 2.4 | 3279 | 28.9 | 13.3 |

What is claimed is:

1. An apparatus for flow injection analysis (FIA) determination by the molybdenum blue complex colorimetric reaction of total inorganic phosphate concentration in an aqueous system containing dissolved inorganic polyphosphate as well as orthophosphate, comprising (1) filter means and three-way valve means for establishing a filtered, continuously flowing sample stream from said aqueous system to waste, from which sample units may be selected at designated intervals; (2) mixing valve means having two switchable modes of operation: (a) when a sample unit is not to be analyzed, two reagent composition streams comprising a color-forming reagent and a reducing agent, are brought together and admixed on a continuous basis; and (b) when a sample unit is to be analyzed, the stream of reducing agent is interrupted and the filtered sample stream is substituted therefor for sufficient time to select a sample unit, which then becomes admixed with the color-forming reagent stream, while bounded in front and behind by said reducing agent stream when the flow of the reducing agent stream is restored, thereby forming a reaction mixture of the sample unit, color-forming reagent and reducing agent; (3) a first conduit means for separately connecting and carrying the sample stream and the two reagent composition streams to said mixing valve means; (4) container means for the two reagent compositions, connected to said mixing valve means by said first conduit means; (5) a second conduit means from said mixing valve means, and eventually to waste, for carrying the reaction mixture stream formed by mixing of the sample stream and the two reagent composition streams during and subsequent to passage through said mixing valve means, said second conduit means being of sufficient length to permit completion of the colorimetric reaction in the reaction mixture stream; (6) heating means through which the second conduit means passes for heating of the reaction mixture stream; (7) colorimetric means through which the second conduit means passes, having a 600-850 nm filter for reading the signal produced by the reaction mixture stream; and (8) means for maintaining a pressure of from 2-10 psi throughout the means comprising the FIA apparatus, whereby the sample, reagent composition, and reagent mixture streams are individually and collectively impelled through said means, eventually to waste.

2. An apparatus according to claim 1 wherein the filter means is a tangential flow bypass membrane filter system; the heating means is an immersion heater; the first and second conduit means are made of polyetheretherketone (PEEK) tubing; and the FIA apparatus additionally includes computer means which process the data from the colorimeter means together with other data which results in calculation of the concentration of total inorganic phosphate contained in the aqueous system from which the sample for testing was obtained.

3. An apparatus for flow injection analysis (FIA) determination by the molybdenum blue complex colorimetric reaction of total inorganic phosphate concentration in an aqueous system containing dissolved inorganic polyphosphates as well as orthophosphate, comprising (1) filter means, selector valve means, and injection valve means for establishing a filtered, continuously flowing sample stream from said aqueous system to waste, from which sample units may be selected at designated intervals for passage through the FIA apparatus, by switching of the injection valve means; (2) said injection valve means recited above, and separate mixing connector means which are connected and operate together so as to have two switchable modes of operation: (a) when a sample unit is not to be analyzed, two reagent composition streams comprising a color-forming reagent and a reducing agent, are brought together and admixed on a continuous basis at and by the mixing connector means, the color-forming reagent flowing directly into said mixing connector means, and the reducing agent flowing into said mixing connector means after first passing through said injection valve means; and (b) when a sample unit is to be analyzed, the stream of reducing agent is interrupted by switching of said injection valve means recited above and the filtered sample stream is substituted therefor for sufficient time to select a sample unit, which then becomes admixed, at said mixing connector means, with the color-forming reagent stream, while bounded in front and behind by said reducing agent stream when the flow of the reducing agent stream is restored by switching of said injection valve means, thereby forming a reaction mixture of the sample unit, color-forming reagent and reducing agent; (3) a first conduit means having two branches for separately connecting and carrying the sample stream and the reducing agent stream to said injection valve means, and from there a single branch to said mixing connector means; and a second conduit means for directly connecting and carrying the color-forming reagent stream to said mixing connector means without passing through said injection valve means; (4) container means for the two reagent compositions, connected to the injection valve means and the mixing connector means by said first and second conduit means as set out above; (5) a third conduit means from the mixing connector means and eventually to waste, for carrying the reaction mixture stream formed by mixing of the sample stream and the two reagent composition streams during and subsequent to passage through said mixing connector means, said third conduit means being of sufficient length to permit completion of the colorimetric reaction in the reaction mixture stream; (6) heating means through which the third conduit means passes for heating of the reaction mixture stream; (7) colorimetric means through which the third conduit means passes, having a 600-850 nm filter for reading the signal produced by the reaction mixture stream; and (8) means for maintaining a pressure of from 2-10 psi throughout the means comprising the FIA apparatus, whereby the sample, reagent composition, and reaction mixture streams are individually and collectively impelled through said means, eventually to waste.

4. An apparatus according to claim 3 wherein the filter means is a targeted flow bypass membrane filter system; the heating means is an immersion heater; the first, second and third conduit means are made of polyetheretherketone (PEEK) tubing; the mixing connector means is a T-connector; and the FIA apparatus additionally includes computer means which process the data from the colorimeter means together with other known data which results in calculation of the concentration of the total inorganic phosphate contained in the aqueous system from which the sample for testing was obtained.

* * * * *